(12) United States Patent
Clayman et al.

(10) Patent No.: US 11,389,264 B2
(45) Date of Patent: Jul. 19, 2022

(54) SAFETY URETERAL ACCESS SHEATH AND INTERVENTIONAL CATHETER INSERTION WITH INTRINSIC AND EXTRINSIC FORCE METERS

(71) Applicant: The Regents of The University of California, Oakland, CA (US)

(72) Inventors: Ralph Clayman, Irvine, CA (US); Kam Kaler, Huntington Beach, CA (US); Michael Klopfer, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 632 days.

(21) Appl. No.: 16/127,996

(22) Filed: Sep. 11, 2018

(65) Prior Publication Data
US 2019/0076209 A1    Mar. 14, 2019

Related U.S. Application Data

(60) Provisional application No. 62/557,628, filed on Sep. 12, 2017.

(51) Int. Cl.
| | | |
|---|---|---|
| *A61B 90/00* | (2016.01) | |
| *A61B 1/00* | (2006.01) | |
| *A61B 1/307* | (2006.01) | |
| *A61M 25/01* | (2006.01) | |
| *A61B 90/92* | (2016.01) | |
| *A61M 25/06* | (2006.01) | |

(52) U.S. Cl.
CPC .......... *A61B 90/06* (2016.02); *A61B 1/00055* (2013.01); *A61B 1/00066* (2013.01); *A61B 1/00128* (2013.01); *A61B 1/00147* (2013.01); *A61B 1/00154* (2013.01); *A61B 1/307* (2013.01); *A61M 25/01* (2013.01); *A61B 90/92* (2016.02); *A61B 2090/032* (2016.02); *A61B 2090/034* (2016.02); *A61B 2090/037* (2016.02); *A61B 2090/064* (2016.02); *A61B 2090/065* (2016.02); *A61B 2090/0807* (2016.02); *A61M 2025/0681* (2013.01)

(58) Field of Classification Search
CPC ..................................................... A61B 1/307
See application file for complete search history.

(56) References Cited

U.S. PATENT DOCUMENTS 7,654,989 B2 *   2/2010   Knapp ................... A61B 1/307
                                                    604/284
2009/0306472 A1 * 12/2009  Filipi .................... A61M 29/00
                                                    600/104

* cited by examiner

*Primary Examiner* — Andrew Yang
(74) *Attorney, Agent, or Firm* — Nguyen Tarbet LLC

(57) ABSTRACT

The invention relates to medical devices and methods of use thereof, such as for example, ureteroscopy. In one embodiment, the device is a safety ureteral access sheath and interventional catheter insertion with a force meter and a force disengagement mechanism. In another embodiment, the invention provides a method of examination or treatment for a condition in a subject, comprising providing a device comprising a ureteral access sheath (UAS) operably linked to a force meter and a force disengagement mechanism, and using the device to examine or treat the subject.

5 Claims, 5 Drawing Sheets

SAFETY URETERAL ACCESS SHEATH AND INTERVENTIONAL CATHETER INSERTION WITH INTRINSIC AND EXTRINSIC FORCE METERS

CROSS-REFERENCE TO RELATED APPLICATIONS

The present application claims the benefit of priority under 35 U.S.C. § 119(e) of provisional application Ser. No. 62/557,628, filed Sep. 12, 2017, the contents of which are hereby incorporated by reference.

FIELD OF THE INVENTION

The invention relates generally to medical devices and methods of use thereof.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Ureteroscopy is an examination or procedure using a ureteroscope, which is an instrument for examining the inside of the urinary tract. The use of a ureteral access sheath is used to establish a conduit during endoscopic urological procedures, so that the passage of instruments into the urinary tract may be facilitated. The use of a ureteral access sheath during ureteroscopy has been beneficial on many levels: decreased cost of the procedure, better ability to clear stones, and less overall trauma to the ureter. However, if too large a sheath is forcefully placed, it causes a splitting of the urothelium resulting in the need for prolonged postoperative internal stinting and the possibility of a ureteral stricture. For example, the porcine ureter splits when forces exceeding 8 Newtons are applied to the sheath. Thus, there is a need in the art for improvements to increase the inherent safety of the uretal access sheath and/or implements to aid the insertion process. This same improvement paradigm transcends uretal access sheath insertions and provides a novel approach to improving safety in which a device, trocar, catheter, or guidewire is passed into the human body.

SUMMARY OF THE INVENTION

Various embodiments include a device comprising a ureteral access sheath (UAS) operably linked to a force meter and a force disengagement mechanism. In another embodiment, the device further comprises a catheter insertion. In another embodiment, the UAS provides passage of an endoscope. In another embodiment, the UAS provides passage of an endoscope. In another embodiment, the UAS provides passage of a ureteroscope. In another embodiment, the force meter is intrinsic to the device. In another embodiment, the force meter is extrinsic to the device. In another embodiment, the force meter is spring loaded. In another embodiment, the degree of force applied to the UAS corresponds to a color marking system in the force meter. In another embodiment, the degree of force applied to the UAS corresponds to one or more chime sounds. In another embodiment, the disengagement mechanism is a magnetic disengagement mechanism. In another embodiment, the disengagement mechanism is a crumpling disengagement mechanism. In another embodiment, the force disengagement mechanism disengages a ring from the UAS if an excessive force is applied. In another embodiment, the excessive force is 8 Newtons or more. In another embodiment, the excessive force is 7 Newtons or more. In another embodiment, the force disengagement mechanism is set by a shimmed magnet and a ferrous ring. In another embodiment, the force disengagement mechanism is in a linear configuration. In another embodiment, the force disengagement mechanism is in a rotary configuration. In another embodiment, the force disengagement mechanism is applied to the UAS on its back end. In another embodiment, the device further comprises a pressure sensitive grip. In another embodiment, the pressure sensitive grip will fail and cannot be advanced further if an unsafe pressure is approached. In another embodiment, the device is described in FIGS. 1, 2, 3, 4 and/or 5 herein. In another embodiment, the device further comprises an operably linked connector, floating shaft, device body, force gauge, maximum force indicator, and indicator. In another embodiment, the device further comprises an operably linked finger grip, UAS device body, UAS shaft, high-K spring, collapsible bellows, force gauge, slide channel, and a magnet and ferrous ring pair. In another embodiment, the UAS is a Leur-Lok interfacing UAS.

Other embodiments include a method of examination and/or treatment for a condition in a subject, comprising providing a device comprising a ureteral access sheath (UAS) operably linked to a force meter and a force disengagement mechanism, and examining and/or treating the subject by utilizing the device. In another embodiment, the condition is related to the urinary tract. In another embodiment, a trocar, catheter, and/or guidewire is passed into the subject. In another embodiment, the examination comprises ureteroscopy. In another embodiment, the force disengagement mechanism is a magnetic mechanism. In another embodiment, the force disengagement mechanism is a crumpling mechanism. In another embodiment, the device is described in FIGS. 1, 2, 3, 4 and/or 5 herein.

Other embodiments include a method of diagnosing susceptibility to a disease in a subject, comprising providing a device comprising a sheath and an insert, wherein the insert will disengage when an excessive amount of force is applied, and diagnosing susceptibility to the disease through an examination of the subject by the device. In another embodiment, the disease is related to the urinary tract. In another embodiment, the device further comprises a force meter. In another embodiment, the device further comprises a force disengagement mechanism. In another embodiment, the device is described in FIGS. 1, 2, 3, 4 and/or 5 herein.

Other features and advantages of the invention will become apparent from the following detailed description, taken in conjunction with the accompanying drawings, which illustrate, by way of example, various embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

Luer-Lok female connector to connect to the male Luer-Lok connector on the stylet on the top of the uretal access sheath device; (2) floating shaft; (3) device body; (4) force gauge; (5) maximum force indicator; (6) red indicator at top of the floating shaft.

Figure 1:
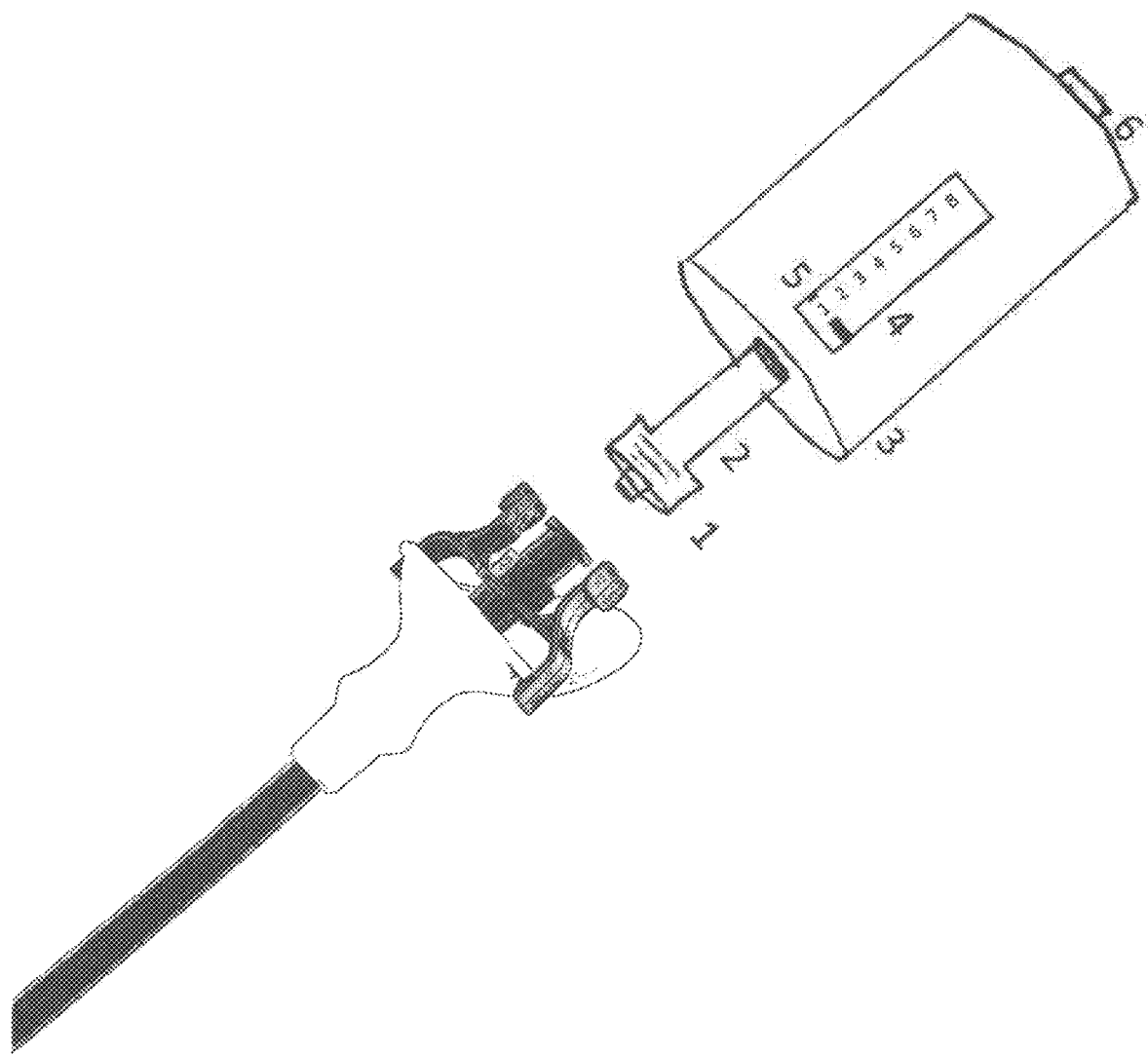
FIG. 1 depicts, in accordance with an embodiment herein, a Luer-Lok interfacing ureteral access sheath force measurement and protection device. Pictured is the following: (1)
Figure 2:
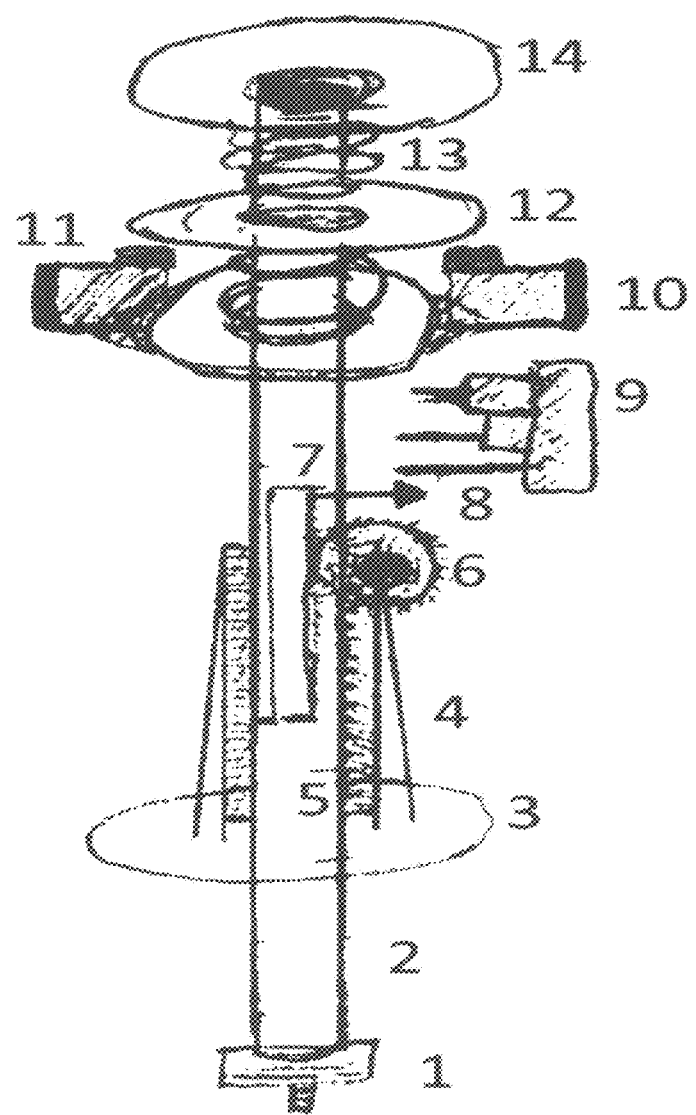

FIG. 2 depicts, in accordance with an embodiment herein, the mechanism of the device pictured in FIG. 1. Pictured is the following: (1) Luer-Lok female connector to connect to the male Luer-Lok connector on the stylet on the top of the uretal access sheath device; (2) floating shaft; (3) device body bottom; (4) floating shaft guide; (5) floating shaft rack gear; (6) meter gear; (7) meter pointer on rack gear; (8) chime striker; (9) chime and resonance cavity; (10) spring base and magnet retainer which is fixed to device body and coaxial with the shaft; (11) magnetic ring; (12) ferrous ring retainer for high-k spring; (13) low-k return spring; (14) device body top.

Figure 3:
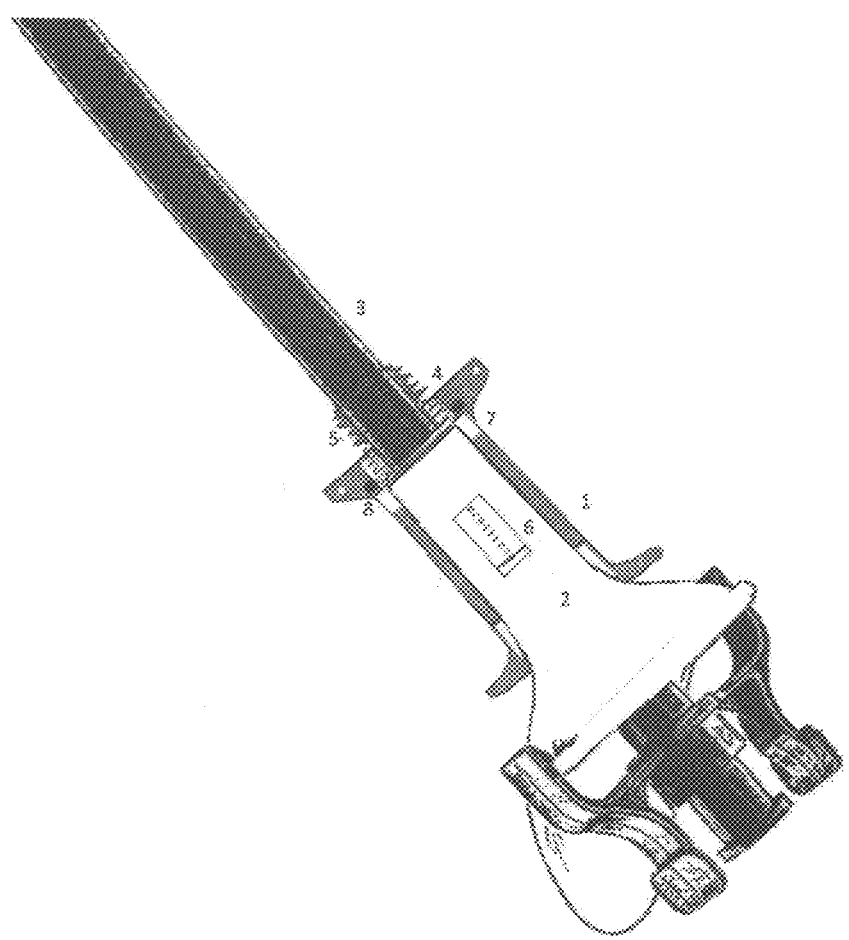

FIG. 3 depicts, in accordance with an embodiment herein, an integrated force measurement and safety release uretal access sheath. Pictured is the following: (1) finger grip; (2) uretal access sheath device body; (3) uretal access sheath shaft; (4) high-K spring; (5) collapsible bellows; (6) force gauge; (7) slide channel; (8) magnet and ferrous ring pair.

Figure 4:
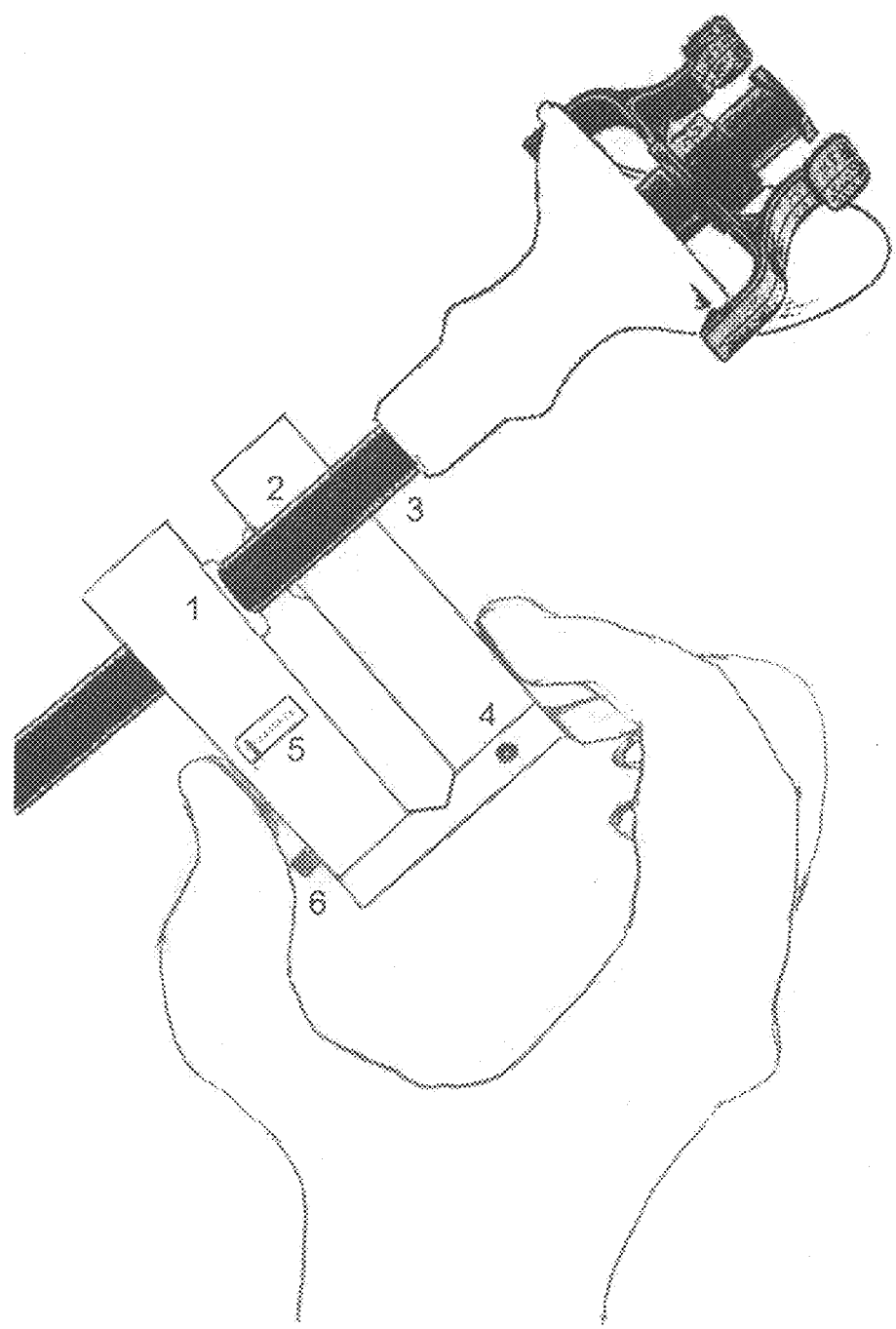

FIG. 4 depicts, in accordance with an embodiment herein, a shaft-coupling embodiment of the device pictured in FIG. 1. Pictured is the following: (1) Controlled forceps arm; (2) idler forceps arm; (3) uretal access sheath shaft; (4) pivot; (5) force gauge; (6) release button.

Figure 5:
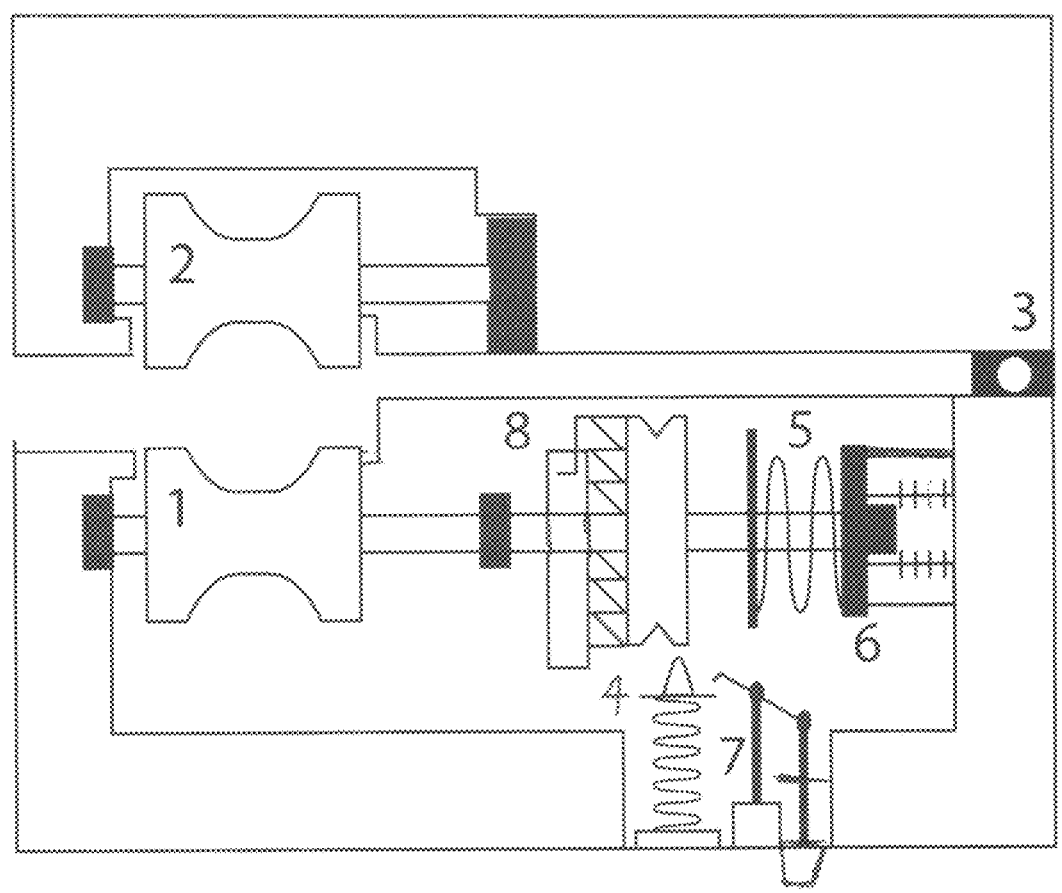

FIG. 5 depicts, in accordance with an embodiment herein, the mechanism of the device pictured in FIG. 4. Pictured is the following: Pliable roller on shaft supported by rotational bearings—connected; (2) Pliable roller on shaft supported by rotational bearings—idler; (3) pivot; (4) force clutch—shifts coaxially as force is increased as sloped teeth un-mesh; (5) high-k spring; (6) threaded support; (7) force clutch retainer and reset button; (8) force gauge.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Hinman's Atlas of Urologic Surgery 3rd Edition, 2012, and Ureteroscopy: Indications, Instrumentation & Technique, 2013 edition, provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As described herein, in accordance with various embodiments, the inventors have developed a safety ureteral access sheath and interventional catheter insertion with intrinsic and/or extrinsic force meters with or without force disengagement mechanisms. Presently, all practitioners in the art place the ureteral access sheath by feel alone, which is prone to human error. The amount of force placed applied on to the shaft during deployment is quite variable, and thereby exposes the patient to the possibility of ureteral injury or rupture. Various embodiments described herein would allow the surgeon, or user, to know the amount of force being applied, depending on the design.

In one embodiment, the present invention provides a sheath with a built in mechanism such that forces on the order of 7-10 Newtons would result in the cessation of forward progress of the sheath thereby avoiding higher and more damaging pressures (FIG. 3). Additionally, in accordance with embodiments herein, the inventors have developed a novel add on device that measures the force applied during insertion and assesses for injuries, wherein 8. Newtons is the threshold force beyond which injury is more likely to occur (FIG. 1 and FIG. 4). In one embodiment, the present invention provides a device that can also be used for diverse interventional radiology procedures in which catheters and sheaths are placed into various vessels (e.g. vascular, biliary, etc.). As readily apparent to one of skill in the art, various embodiments herein could be applied to the passage of other catheters or guidewires, and the invention is in no way only limited to use of a ureteroscope, as indeed it could be applied not only to the passage of a sheath but also to the passage of an endoscope itself. In one embodiment, the present invention provides a medical device to preclude excessive pressure being applied to position and/or deploy an ureteral access sheath (UAS), a catheter (example, Foley), and/or a guidewire (example, during a vascular procedure).

In one embodiment, the present invention provides a ureteral access sheath (UAS). In another embodiment, the shaft of the ureteral access sheath would be outfitted with a place where the surgeon would place his/her fingers, such as a finger grip of the UAS force meter, so that the user could push it up the ureter and position it. In another embodiment, the finger grip of the UAS force meter would be its own separate piece thereby making it adaptable to other devices, catheters, endoscopes, sheaths, or guidewire. In another embodiment, the finger grip of the UAS force meter would be spring-loaded. In another embodiment, on the shaft of the ureteral access sheath would be three colored rings, for example, green, yellow, and red, to indicate the level of force applied and when caution (i.e. yellow) is indicated and at what point further force would be beyond 7 Newtons (i.e. red). As the surgeon pushes on the sheath, the spring loaded portion would move slightly in proportion to the pressure being applied to push the sheath up the ureter. In another embodiment, if the ring moves into the yellow area, for example, this would correspond to a specified level of force ((Newtons (N)) or pounds-force or grams-force. Color indicators would be visible on the force gauge on the device. Or, for example, in another embodiment, the red ring would reflect a very high force, in order of 7-10 Newtons of force and would be an indicator that too much force is being applied and could result in injury.

In another embodiment, the device can be constructed such that the ring will disengage applied force from the sheath if 8 Newtons is approached thereby precluding the possibility of ureteral wall splitting from passage of too large a sheath. In another rendition, the device could be applied to the obturator of the sheath on its back end such that excessive pressure results in the device failing such that forward motion of the device would be halted, in for example, a crumpling mechanism such that if the user applied a certain level of force (pre-defined between 7-10 N) the obturator would buckle or crumple. In accordance with various embodiments herein, a mechanism permitting easily felt buckling and crumpling could alert the surgeon while limiting applied force and could be applied to any part of the UAS. For example, the shaft of the UAS could buckle if there was there was too much frictional force applied during insertion (from shear or frictional forces) and the same could be applied for the tip of the obturator. In accordance with one embodiment herein (see figure herein describing Renderings of the Safety Ureteral Access Sheath and Interventional Catheter Insertion with Intrinsic and Extrinsic Force Meters).

In accordance with various embodiments herein, the inventors have developed a safety ureteral access sheath that is designed to preclude serious damage to the ureter during its passage. In one embodiment, the sheath is equipped with a pressure sensitive grip such that when the surgeon passes the sheath into the urethra, bladder, and/or ureter, if an unsafe pressure is approached, the grip fails and the sheath cannot be advanced any further. In one embodiment, this is a clear indication to the surgeon to downsize the sheath thereby assuring that the ureter does not get damaged. In another embodiment, this safety mechanism is applied to the shaft of the ureteral access sheath and the obturator. In another embodiment, this safety mechanism could be used in other medical devices and specialties, such as interventional radiology where catheters are inserted in a similar mechanism over guidewires.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Ureteral Access Sheath (UAS)

The shaft of the ureteral access sheath (UAS) would be outfitted with a place where the surgeon would place his/her fingers ("finger grip of the UAS force meter") in order to push it up the ureter and position it. The finger grip of the UAS force meter would be its own separate piece and would be spring loaded; on the shaft of the ureteral access sheath would be colored rings (e.g. green, yellow, and red) to indicate the level of force applied. As the surgeon pushes on the sheath, the spring loaded portion would move slightly in proportion to the pressure being applied to push the sheath up the ureter. If the ring moves into the yellow area, this would correspond to a specified level of force measured in Newtons (N) or pounds-force or grams-force; the red ring would reflect a very high force, in order of 7-10 Newtons of force and would be an indicator that too much force is being applied and likely result in injury. As the force is increased, chimes sound indicating the level of force in a device similar to that of a music box (FIG. 2). Alternatively the device can be constructed such that the ring will disengage from the sheath if 8 N is approached thereby precluding the possibility of ureteral wall splitting from passage of too large a sheath. A mechanism for this design is shown in three embodiments in FIG. 2, FIG. 3, and FIG. 5. A shimmed magnet and ferrous ring are used to set disengagement force. Once this force is met, the magnet disengages from the ferrous ring and the floating component connected to the uretal access sheath body is released. This release of force both disengages dangerous force and alerts the surgeon to the high force applied. This mechanism is demonstrated in both linear (FIG. 2 and FIG. 3) and rotary (FIG. 5) configurations. In another rendition, the same device could be applied to the obturator of the sheath on its back end such that excessive pressure results in the device failing such that forward motion of the device would be halted (e.g. a crumpling mechanism such that if the user applied a certain level of force (pre-defined between 7-10 N), the obturator would buckle or crumple. This same mechanism of buckling and crumpling is an alternative to a magnetic disengagement and could be applied to any part of the UAS. For example, the shaft of the UAS could buckle if there were too much frictional force applied during insertion (from shear or frictional forces) and the same could apply for the tip of the obturator. For example, see figures herein.

The Safety Ureteral Access Sheath with intrinsic and/or extrinsic force meters is designed to preclude serious damage to the ureter during its passage. The sheath is equipped with a pressure sensitive grip such that when the surgeon passes the sheath into the urethra, bladder, and ureter, if an unsafe pressure is approached, the grip fails and the sheath cannot be advanced any further. This is a clear indication to the surgeon to downsize the sheath thereby assuring that the ureter does not get damaged. This safety mechanism could be applied to the shaft of the ureteral access sheath and also to the obturator. This same safety mechanism could be used in other medical devices and specialties, especially interventional radiology where catheters are inserted over a guidewire.

Example 2

Disadvantages of Alternatives in the Art

Presently, all practitioners in the art place the ureteral access sheath by feel alone, which is prone to human error. The amount of force applied to the shaft during deployment is quite variable, and thereby exposes the patient to the possibility of ureteral injury. The device described herein would allow the surgeon, or user, to know the amount of force being applied, depending on the design, thereby precluding the use of potentially damaging force.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A device, comprising: a ureteral access sheath (UAS) operably linked to a force meter and a force disengagement mechanism wherein the device further comprises an operably linked connector, floating shaft, device body, force gauge, maximum force indicator, and indicator.

2. A device, comprising: a ureteral access sheath (UAS) operably linked to a force meter and a force disengagement mechanism wherein the force disengagement mechanism is a magnetic disengagement mechanism.

3. The device of claim 2, wherein the device further comprises an operably linked finger grip, UAS device body, UAS shaft, high-K spring, collapsible bellows, force gauge, slide channel, and a magnet and ferrous ring pair.

4. A device comprising: a ureteral access sheath (UAS) operably linked to a force meter and a force disengagement mechanism wherein the force disengagement mechanism is set by a shimmed magnet and a ferrous ring.

5. The device of claim 4, wherein the device further comprises an operably linked finger drip, UAS device body, UAS shaft, high-K spring, collapsible bellows, force gauge, and a slide channel.

* * * * *